United States Patent
Govari et al.

(10) Patent No.: US 10,952,637 B2
(45) Date of Patent: Mar. 23, 2021

(54) RADIOFREQUENCY (RF) TRANSMISSION SYSTEM TO FIND TISSUE PROXIMITY

(71) Applicant: BIOSENSE WEBSTER (ISRAEL) LTD., Yokneam (IL)

(72) Inventors: Assaf Govari, Haifa (IL); Andres Claudio Altmann, Haifa (IL); Vadim Gliner, Haifa (IL); Alon Boumendil, Givat Nili (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 111 days.

(21) Appl. No.: 16/141,125

(22) Filed: Sep. 25, 2018

(65) Prior Publication Data

US 2020/0093398 A1 Mar. 26, 2020

(51) Int. Cl.
A61B 5/107 (2006.01)
A61B 5/06 (2006.01)
A61B 5/00 (2006.01)
A61M 25/01 (2006.01)

(52) U.S. Cl.
CPC ............ *A61B 5/068* (2013.01); *A61B 5/1076* (2013.01); *A61B 5/1077* (2013.01); *A61B 5/4836* (2013.01); *A61B 5/6869* (2013.01); *A61B 5/7278* (2013.01); *A61B 5/743* (2013.01); *A61B 2562/0257* (2013.01); *A61M 2025/0166* (2013.01)

(58) Field of Classification Search
CPC ..... A61B 5/068; A61B 5/1076; A61B 5/1077; A61B 5/4836; A61B 5/6869; A61B 5/7278; A61B 5/743; A61B 2562/0257; A62M 2025/0166
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |

(Continued)

FOREIGN PATENT DOCUMENTS

| | | |
|---|---|---|
| EP | 2338419 A1 | 6/2011 |
| WO | WO 96/05768 A1 | 2/1996 |
| WO | WO2018146613 A2 | 8/2018 |

OTHER PUBLICATIONS

Pending U.S. Appl. No. 15/610,865, filed Jun. 1, 2017.

(Continued)

*Primary Examiner* — Ankit D Tejani
*Assistant Examiner* — Joshua Brendon Solomon

(57) ABSTRACT

A method includes receiving, from a probe that comprises electrodes and is positioned inside a cavity in an organ of a patient, (i) proximity signals indicative of proximity of the electrodes to a wall of the cavity, and (ii) position signals indicative of positions of the electrodes within the cavity. Based on the proximity signals and the position signals, at least a portion of a volume of the cavity is represented by a sphere model including multiple spheres. An estimated contour of the wall of the cavity is calculated based on the sphere-model. The estimated contour of the wall is presented to a user.

10 Claims, 3 Drawing Sheets

(56) References Cited

U.S. PATENT DOCUMENTS

| | | |
|---|---|---|
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| 2001/0009976 A1 | 7/2001 | Panescu et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0116576 A1 | 6/2006 | McGee et al. |
| 2006/0287649 A1 | 12/2006 | Ormsby et al. |
| 2007/0049826 A1* | 3/2007 | Willis ................ A61B 1/00147 600/439 |
| 2012/0158011 A1 | 6/2012 | Sandhu et al. |
| 2015/0265341 A1* | 9/2015 | Koblish ............. A61B 18/1492 600/509 |
| 2017/0348049 A1* | 12/2017 | Vrba ................. A61B 18/1492 |

OTHER PUBLICATIONS

Pending U.S. Appl. No. 15/991,291, filed May 29, 2018.
European Search Report for corresponding EPA No. dated 19199252.8 dated Feb. 12, 2020.

\* cited by examiner

RADIOFREQUENCY (RF) TRANSMISSION SYSTEM TO FIND TISSUE PROXIMITY

FIELD OF THE INVENTION

The present invention relates generally to invasive medical instruments, and particularly to methods of electroanatomical mapping using intra-body probes.

BACKGROUND OF THE INVENTION

Various techniques were proposed for electroanatomical mapping of cardiac tissue. For example, U.S. Patent Application Publication 2006/0116576 describes systems and a method for navigating a catheter relative to a heart. A mark, such as a point or line, representing an anatomical region of interest, such as cardiac tissue targeted for treatment, is displayed on a representation of the anatomical body. The positions of the medical probe and the mark are determined within a three-dimensional coordinate system, and the proximity between the medical probe and the mark determined based on these positions. This proximity can then be indicated to a user, e.g., using graphics, text, or audible sounds.

As another example, U.S. Patent Application Publication 2001/0009976 describes a system that records use of a structure deployed in operative association with heart tissue in a patient. An image controller generates an image of the structure while in use in the patient. An input receives data including information identifying the patient. An output processes the image in association with the data as a patient-specific, data base record for storage, retrieval, or manipulation.

U.S. Patent Application Publication 2012/0158011 describes a robotic catheter control system that includes a proximity sensing function configured to generate a proximity signal that is indicative of the proximity of the medical device such as an electrode catheter to a nearest anatomic structure such as a cardiac wall. The control system includes logic that monitors the proximity signal during guided movement of the catheter to ensure that unintended contact with body tissue is detected and avoided. The logic includes a means for defining a plurality of proximity zones, each having associated therewith a respective proximity (distance) criterion.

U.S. Patent Application Publication 2006/0287649 describes a radio-frequency based catheter system and method for ablating biological tissues within the body vessel of a patient that comprises a radio-frequency ("RF") generator for selectively generating a high frequency RF energy signal in a deployable catheter having an RF transmission line, an RF antenna mounted on the distal portion of the catheter, and a temperature sensor also mounted on a distal portion of the catheter for detecting temperature adjacent an ablation site. The shapeable catheter apparatus may carry one or more intracardiac electrocardiogram (ECG) electrodes to permit physicians to obtain both optimum tissue proximity and electrical conductive activities before and after tissue ablation.

SUMMARY OF THE INVENTION

An embodiment of the present invention provides a method including receiving, from a probe that includes electrodes and is positioned inside a cavity in an organ of a patient, (i) proximity signals indicative of proximity of the electrodes to a wall of the cavity, and (ii) position signals indicative of positions of the electrodes within the cavity. Based on the proximity signals and the position signals, at least a portion of a volume of the cavity is represented by a sphere model including multiple spheres. An estimated contour of the wall of the cavity is calculated based on the sphere-model. The estimated contour of the wall is presented to a user.

In some embodiments, calculating the estimated contour includes identifying, in the sphere model, directions along which sizes of the spheres decrease monotonically, and calculating the estimated contour depending on the directions.

In some embodiments, calculating the estimated contour includes finding intersections between smallest-size spheres in the sphere model, and defining the estimated contour to contain the intersections.

In an embodiment, representing the volume by the sphere model includes scaling radiuses of the spheres based on a subset of the proximity signals and the position signals, which were produced while one or more of the electrodes were in physical contact with the wall of the cavity. In an embodiment, scaling the radiuses includes scaling the radiuses of the spheres based on a known geometry of the probe.

In some embodiments, receiving the proximity signals includes receiving bi-polar electrical signals, exchanged between the electrodes at one or more radiofrequency ranges.

There is additionally provided, in accordance with an embodiment of the present invention, a system including an interface and a processor. The interface is configured to receive, from a probe that includes electrodes and is positioned inside a cavity in an organ of a patient, (i) proximity signals indicative of proximity of the electrodes to a wall of the cavity, and (ii) position signals indicative of positions of the electrodes within the cavity. The processor is configured to represent at least a portion of a volume of the cavity by a sphere model including multiple spheres, based on the proximity signals and the position signals. The processor is further configured to calculate an estimated contour of the wall of the cavity based on the sphere-model, and to present the estimated contour of the wall to a user.

The present invention will be more fully understood from the following detailed description of the embodiments thereof, taken together with the drawings in which:

DETAILED DESCRIPTION OF EMBODIMENTS

Overview

Figure 1:
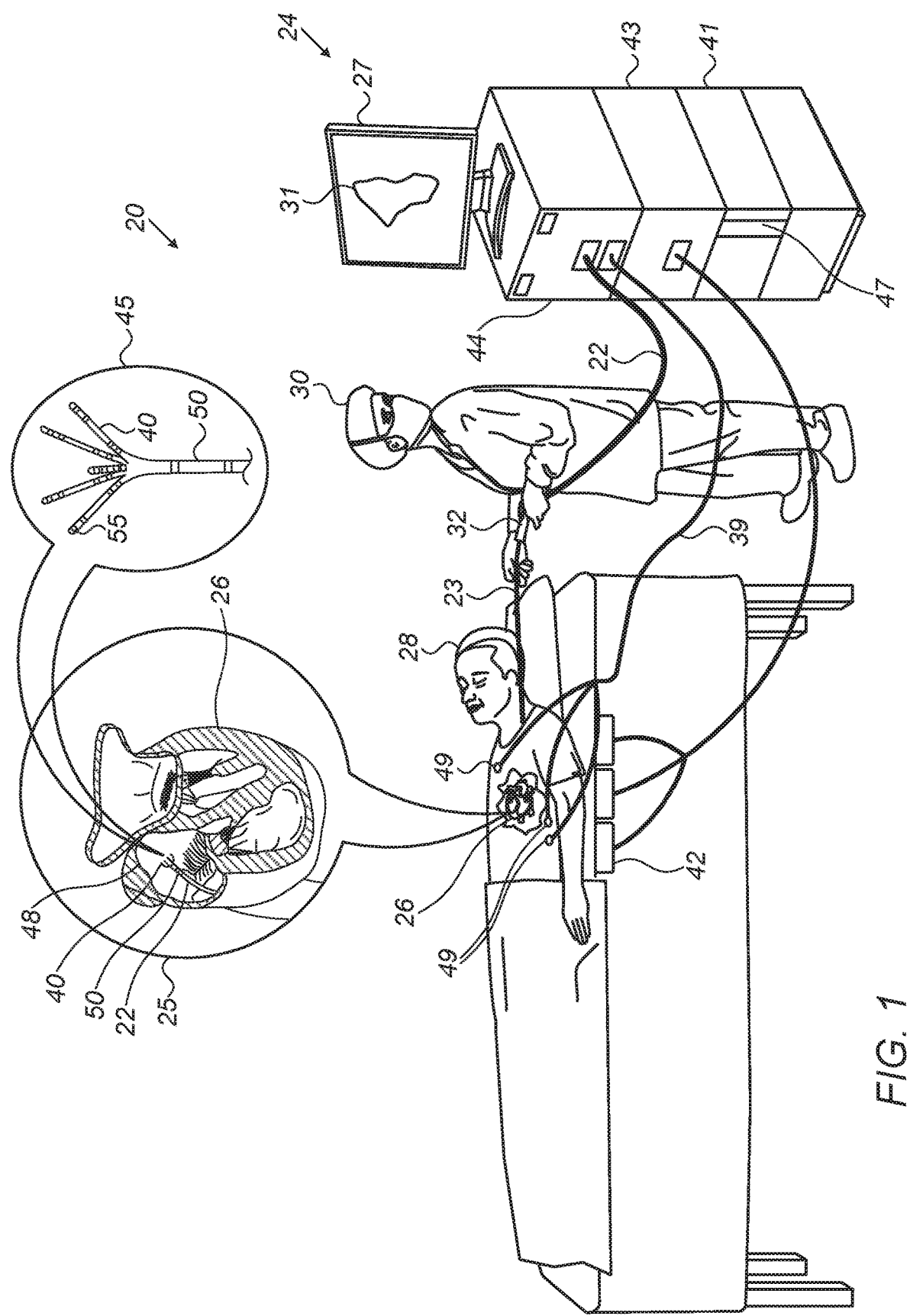
FIG. 1 is a schematic, pictorial illustration of a system for electro-anatomical mapping, in accordance with an embodiment of the present invention.

Embodiments of the present invention that are described hereinafter provide a radiofrequency (RF) transmission system and method for estimating proximity of tissue of a cavity wall of an organ of a patient to a catheter inside the cavity. The disclosed method relies on the typically higher impedance of tissue as compared to blood, especially in the low RF frequency range of several kHz. Thus, measured impedances increase as the catheter nears a cavity wall, indicating closer proximity of tissue.

In some embodiments, during an electro-anatomical mapping session of a cavity, such as a cardiac chamber, a catheter having multiple distal-electrodes is positioned in the cavity. The disclosed system measures bi-polar impedances (impedances between pairs of distal-electrodes) in one or more RF frequency ranges. A processor uses the measured impedances, along with a prior calibration process, to estimate the proximity of tissue to the catheter. The mapping involves three stages:

Data Acquisition Stage

In some embodiments, a processor is configured to represent at least a portion of a cavity volume of an organ of a patient with a sphere-model. The sphere-model comprises spheres of different sizes, with the smaller spheres located closer to the surface. The processor identifies directions along which the sizes of spheres decrease monotonically. Based on intersections between the smallest spheres at the respective indicated directions, the processor calculates an estimated contour along the surface of the cavity wall.

In some embodiments, while the catheter is moved across the cardiac chamber, a position-tracking system measures various positions P of the catheter distal end. The system uses, for example, a magnetic sensor that is fitted at the distal end of the catheter. The sensor outputs, in response to externally-applied magnetic fields, position signals which are received by a processor of the position-tracking system. Based on the position signals, the processor derives catheter positions P inside the cardiac chamber.

In parallel, the system measures proximity signals, such as electrical bi-polar signals between one or more pairs of the distal-electrodes that are fitted on the distal end of the catheter. Based on the bi-polar signals, which, as noted above, are indicative of the proximity of wall tissue to the catheter, and based on the measured positions P, a processor constructs a cavity sphere-model. The sphere-model represents at least a portion of the cavity volume by a set of partially overlapping spheres $\{(P, \rho)\}$. Each sphere $(P, \rho)$ in the model is described by (a) a known location, P, of its center, and, (b) a yet unscaled radius, $\rho$, which is indicative of a distance between location P and the cavity wall. In an embodiment, (i) the magnetically measured positions P are the centers P of the spheres $\{(P, \rho)\}$, and (ii) the unscaled radiuses, $\rho$, are derived from the electrically measured impedances, such that as impedance becomes higher $\rho$ becomes smaller.

In the disclosed cavity representation, a sphere $(P, \rho)$ which is located deeper inside the cavity (i.e., further away from a cavity wall) will typically be larger than a sphere located closer to a wall (i.e., deeper spheres have a larger $\rho$). The transition from larger to smaller diameter spheres is typically gradual and "smooth."

Calibration Stage

To scale radiuses $\rho$ into absolute values R, (i.e., to calibrate $\rho$), the processor uses instances when the distal end comes into physical contact with cavity wall tissue. When an electrode pair comes in physical contact with a location T over cavity wall tissue, the processor correlates the bi-polar signals with a geometrically known distance $R_T$ between the electrode-pair and the magnetic sensor, which is at a respective location $P_T$. Distance $R_T$ is known from the dimensions of the catheter distal end, yielding a reference sphere $(P_T,$ $R_T)$ for scaling the radiuses of set $\{(P, \rho)\}_T$. In an embodiment, the scaling is performed in real time.

In some embodiments, the processor scales the radiuses of the sphere model in a certain portion of the cavity based on a location T in which the catheter is known to have made physical contact with the cavity wall (tissue). To detect physical contact at location T, the system may employ the distal electrodes and/or a dedicated sensor, such as a contact-force sensor, or other methods and means known in the art.

In an embodiment, a multiplicity of distinct calibration points T is used as the catheter moves inside the cardiac chamber. In this way, multiple sphere-models, each localized about a distinct contact location, are combined into a global sphere-model that represents a larger portion of the cardiac chamber, possibly the entire chamber.

Mapping Stage

Once calibration has conducted, i.e., after the processor constructed the calibrated sphere-model about a location T, the processor identifies a direction, in the sphere representation, along which a smooth transition occurs from larger spheres to the smallest spheres. This direction points toward the location of local wall tissue, in that the smallest spheres are those nearest to wall tissue, as explained above.

At this point the processor identifies segments defined by the smallest overlapping spheres that are approximately located on the cavity wall in the vicinity of location T.

In some embodiments, the processor further analyses the derived set of segments so as to locally map a continuous cavity wall in the vicinity of location T (e.g., by interpolating between the segments).

In an embodiment, the disclosed system and method may then generate an electro-anatomical map of the cardiac chamber. The map may be presented to a user, e.g., a physician.

The Processor is programmed in software containing a particular algorithm that enables the processor to conduct each of the processor related steps and functions outlined above.

The disclosed RF transmission system and method for estimating tissue proximity is capable of rapidly providing an electro-anatomical model of at least a portion of a cardiac cavity. Combined with minimal perturbation to cardiac tissue achieved by using low-voltage, high-frequency, electrical signals (i.e., far above any bio-physiological activation frequency), the disclosed system and method may give a physician an efficient and safe means of obtaining clinical information to support treatment decisions, such as how to inhibit an arrhythmia.

System Description

FIG. 1 is a schematic, pictorial illustration of an electro-anatomical mapping system 20, in accordance with an embodiment of the present invention. As seen, a physician 30 navigates a PENTARAY® catheter 40 (made by Biosense-Webster, Irvine, Calif.), seen in detail in inset 45, to a target location in a heart 26 of a patient 28 by manipulating shaft 22 using a manipulator 32 near the proximal end of the catheter and/or deflection from a sheath 23.

Catheter 40 is inserted, in a folded configuration, through sheath 23, and only after sheath 23 is retracted does catheter 40 regain its intended functional shape. By containing catheter 40 in a folded configuration, sheath 23 also serves to minimize vascular trauma on its way to the target location.

FIG. 1 depicts a physician 30 using catheter 40, seen in inset 25, to perform electro-anatomical mapping of a cavity of heart 26, having a cavity wall 48, of a patient 28. In some embodiments, system 20 determines the position and/or the proximity of catheter 40 to cardiac wall 48 tissue in a cavity of heart 26, as described below.

Catheter 40 incorporates a magnetic sensor 50 on a shaft 22. Catheter 40 further comprises one or more arms, which may be mechanically flexible, to each of which are coupled one or more distal-electrodes 55, as seen in inset 45. Magnetic sensor 50 and distal-electrodes 55 are connected by wires running through shaft 22 to various driver circuitries in a console 24.

In some embodiments, system 20 comprises a magnetic-sensing sub-system to estimate a position of catheter 40 inside a cardiac chamber of heart 26. Patient 28 is placed in a magnetic field generated by a pad containing magnetic field generator coils 42, which are driven by unit 43. The magnetic fields generated by coils 42 generate position signals in a magnetic sensor 50, which are then provided as corresponding electrical inputs to a processor 41, which uses these to calculate the position of catheter 40.

The method of position sensing using external magnetic fields and sensor 50 is implemented in various medical applications, for example, in the CARTO™ system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 41, typically a general-purpose computer, is further connected via suitable front end and interface circuits 44, to receive signals from surface-electrodes 49. Processor 41 is connected to surface-electrodes 49 by wires running through a cable 39 to the chest of patient 28. In some embodiments, processor 41 estimates the position of catheter 40 inside a cavity by correlating electrical position signals received from either distal-electrodes 55 and/or surface-electrodes 49 with position-calibrated electrical signals acquired previously. The method of electrode position sensing using calibrated electrical signals is implemented in various medical applications, for example in the CARTO™ system, produced by Biosense-Webster, and is described in detail in U.S. Pat. Nos. 7,756,576, 7,869,865, 7,848,787, and 8,456,182, whose disclosures are all incorporated herein by reference.

In some embodiments, during a mapping procedure, distal-electrodes 55 acquire and/or inject radiofrequency (RF) bi-polar signals (i.e., differential electrical signals between pairs of distal-electrodes 55). Signals traveling at least partially through the tissue of wall 48 are typically more attenuated than those traveling through the blood of heart 26. A processor 41 receives the various RF bi-polar proximity signals via an electrical interface 44, and uses bio-impedance information contained in these signals to construct an electro-anatomical proximity map of the cavity, as further elaborated below. During and/or following the procedure, processor 41 may display electro-anatomical proximity map 31 on a display 27.

In some embodiments, processor 41 is further configured to estimate and verify the quality of physical contact between each of distal-electrodes 55 and wall 48 (i.e., the surface of the cardiac cavity) during measurement, so as to correlate the RF bi-polar proximity indicative signals with known distances. Using the correlated bi-polar proximity signals, and the respective positions measured by sensor 50, processor 41 constructs a cavity sphere-model which is used, for example, to map at least a portion of heart 26, as described below.

In an embodiment, the processor indicates a physical contact based on signals received from one or more contact force sensors that are fitted at the distal end of catheter 40. In another embodiment, the indication of physical contact is based on the frequency response of the impedances sensed by distal-electrodes 55. Such a method and technique is described in U.S. patent application Ser. No. 15/991,291, filed May 29, 2018, entitled "Touch detection Based on Frequency Response of Tissue," which is assigned to the assignee of the present patent application and whose disclosure is incorporated herein by reference.

In another embodiment, processor 41 is configured to determine whether one or more flexible arms of a multi-arm distal end of catheter are in physical contact with wall 48 tissue based on identifying geometrical flexion of the arms. Techniques of this sort are described, for example, in U.S. patent application Ser. No. 15/610,865, filed Jun. 1, 2017, entitled "Using a Piecewise-Linear Model of a Catheter Arm to Identify Contact with Tissue," which is assigned to the assignee of the present patent application and whose disclosure is incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm that enables processor 41 to perform the disclosed steps, comprising calculations of proximities and positions, calibrations, and calculating the cavity surface, as further described below.

The example illustration shown in FIG. 1 is chosen purely for the sake of conceptual clarity. FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of wall 48 tissue of heart 26 using part of distal-electrodes 55.

Other types of sensing and/or therapeutic catheters, such as DECANAV®, SMARTTOUCH®, and LASSO® (all produced by Biosense-Webster) may equivalently be employed.

RF Transmission System to Find Tissue Proximity

Figure 2A:
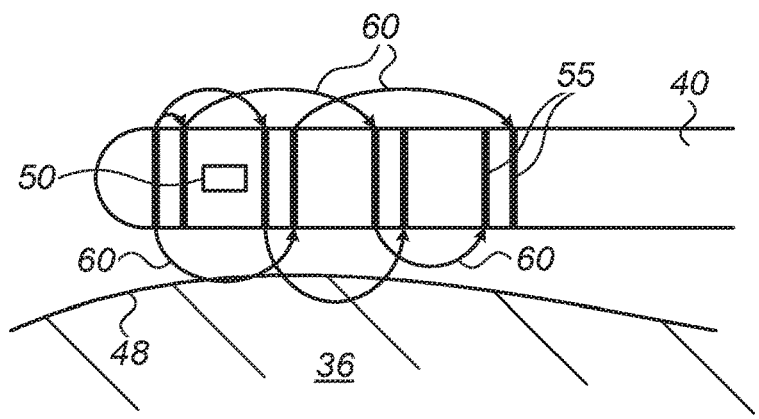
FIGS. 2A and 2B are side-views of a distal end of a catheter performing tissue proximity measurements, in accordance with embodiments of the present invention.
Figure 2B:
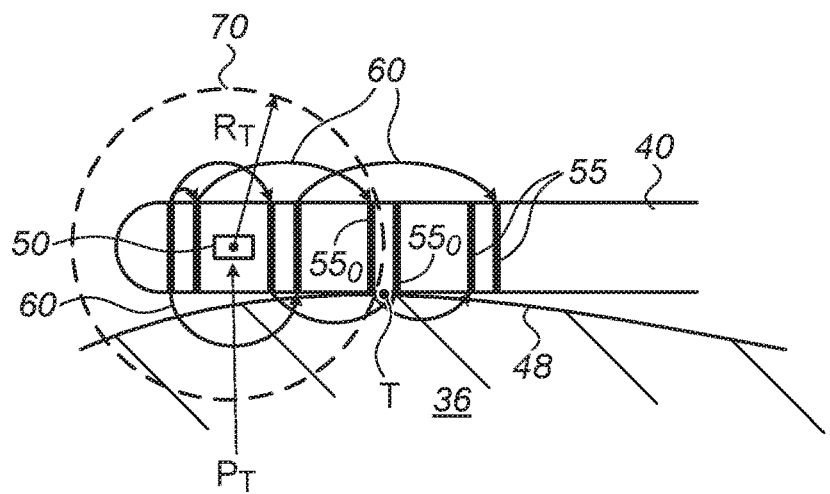

FIGS. 2A and 2B are side-views of a distal end of catheter 40 performing tissue proximity measurements, in accordance with embodiments of the present invention. The catheter distal end is immersed in the blood pool of a cardiac cavity, in the vicinity of a cavity wall 48 of tissue 36.

Data Acquisition Stage

FIG. 2A shows a focal catheter, such as the DECANAV® catheter, which comprises multiple distal-electrodes 55. In an embodiment, distal-electrodes 55 are used to inject, and receive, bi-polar currents (shown schematically as curved arrows 60) at different RF frequency ranges. As seen, some of the electrical paths pass partly in tissue, whereas others pass entirely in blood.

In an embodiment, the process is preset, in the sense that injection and receiving electrodes are selected in advance, as are the frequencies and driving voltages of the currents provided to the injection electrodes.

In some embodiments, the different electrical frequency ranges comprise the ranges of 1-4 kHz and 12-100 kHz. The reason for using two different frequency ranges is that impedance at the 12-100 kHz range is practically insensitive to tissue 36, whereas signals at the 1-4 kHz range show measurable sensitivity to tissue 36. Using the high frequency as reference, small changes in the low-frequency impedances, i.e., as a function of proximity of tissue, can be accurately resolved.

In an embodiment, as catheter 40 moves within the cardiac cavity, processor 41 receives impedance measurements measured between pairs of distal-electrodes 55. Each impedance measurement depends on the transmitting and receiving electrodes, the injection frequencies and voltages, as well as the intervening material (blood and/or tissue). Typically, tissue has a higher impedance than blood, especially in the lower frequency range, so that impedances are generally higher if the electrodes are in close proximity to wall 48 of tissue 36, and vice versa. The dependence of impedances on frequency and on blood and/or tissue, in an embodiment, is provided in U.S. patent application Ser. No. 15/991,291, cited above.

Processor 41 arranges the bi-polar impedances in matrices [M]. Processor 41 correlates each matrix [M] with a respective position P measured by position sensor 50 at which the bi-polar impedances are measured. A set of ordered pairs $\{(P, [M])\}$ is stored by processor 41 in a memory 47. Each bi-polar impedance signal matrix [M] is related to an unscaled wall tissue proximity ρ to the catheter. Hence, at this stage, the processor holds a sphere-model which comprises a set $\{(P, ρ)\}$, with radiuses ρ that are not to scale.

Calibration Stage

FIG. 2B shows an instance in which catheter 40 comes into contact with the cavity wall 48 at a contact point T. The occurrence of physical contact may be determined by any suitable sensor, for example by a force measured by a force sensor in catheter 40, and/or a change of impedance between selected distal-electrodes 55. (FIG. 2B assumes that contact is at two adjacent electrodes $55_0$.)

At contact, the processor scales a respective distance ρ between the contacting tissue wall 48 at contact point T and location sensor 50 in the catheter into $R_T$ (based on catheter geometry, as explained above), yielding a calibrating sphere $(P_T, R_T)$.

Based on the calibration at location T, the processor constructs a correlated pair $(R_T, [M]_T)$, after which the processor scales distances ρ correlated with previous matrices [M] measured in the vicinity of contact point T, to produce a locally scaled set of spheres $\{(P, R)\}_T$.

As indicated above, only the distance $R_T$ to wall 48 tissue, not the direction to the tissue wall, is known, and this distance defines a sphere 70 of radius R around a location $P_T$ of sensor 50, as is illustrated in FIG. 2B. (FIG. 3 describes how processor 40 determines a direction to tissue 36.)

In an embodiment, the described calibration process is repeated as catheter 40 touches tissue at distinct locations $\{T\}$ in the chamber. The resulting local sphere-models $\{(P, R)\}_T$, are subsequently used to estimate cavity wall proximity in a vicinity of each contact location T∈$\{T\}$. As further described below, the disclosed calibration is valid in a region localized about a respective contact point T. Mapping an entire cavity requires multiple contact points.

The illustrations in FIGS. 2A and 2B are brought by way of example. As another example, in some embodiments, distal end 40 is part of a multi-arm catheter (e.g., an arm). In another embodiment, the disclosed tissue-proximity estimation method is applied using a Basket-type catheter distal end. In an alternative to a current injection acquisition method, bi-polar electrical potentials 60a are applied between pairs of distal-electrodes 55 at different frequencies, and the respective impedances are then measured.

Mapping Stage

Figure 3:
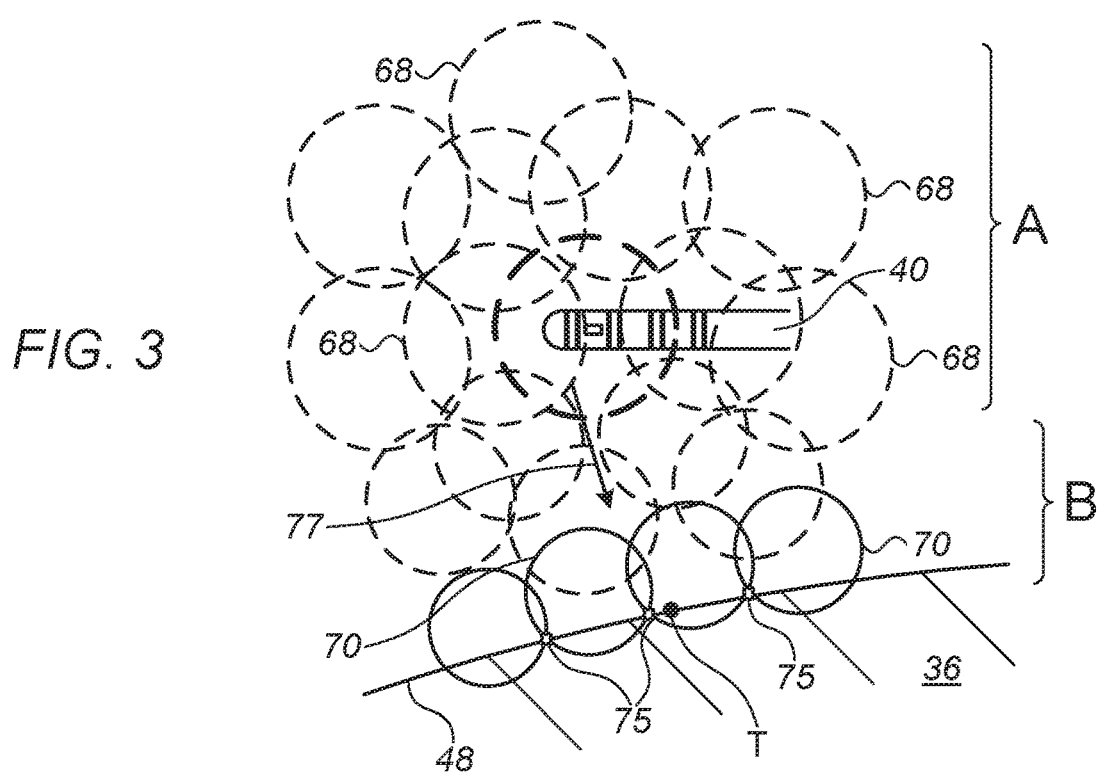
FIG. 3 is a schematic, pictorial illustration of a geometric construction of a localized cavity sphere-model, in accordance with an embodiment of the present invention.

FIG. 3 is a schematic, pictorial illustration of a geometric construction of a localized cavity sphere-model, in accordance with an embodiment of the present invention. During, for example, an investigative electro-anatomical mapping session based on signals acquired using catheter 40, processor 41 constructs a local set of calibrated spheres $\{(P, R)\}_T$, i.e., spheres 68 and spheres 70, in the vicinity of location T, over cavity wall 48.

In an embodiment, an inclusion criteria for a sphere to be part of the local set $\{(P, R)\}_T$, is based, for example, on a position P being, at most, a given distance Γ from a position $P_T$ used for scaling the radiuses. Therefore, FIG. 3 describes only a cavity sphere-model localized (e.g., in the Γ sense) about a given physical contact location T.

The cavity sphere-model can cover a larger portion of the cavity, and up to the entire cavity, if, for example, a sufficient number of distinct contact locations T are recorded over the entire cavity wall during calibration, and a collection of separate sphere-models (e.g., separated from each other by a distance Γ) are obtained.

For regions closer the center of the cavity, approximately equidistant from the cavity walls, a respective set of spheres 68 have approximately equal diameters. This is indicated schematically as a region A of FIG. 3, where the circles (spheres) will typically have larger diameters than those shown.

Radiuses of spheres 70 at points P closer to the wall will typically be smaller than those further away from wall 48, as in a shown in FIG. 3 as region B. The gradual transition from the larger to smaller diameter spheres defines a direction 77 where cavity wall 48 exists.

Outmost intersection segments 75 (shown as points 75) of partially overlapping smallest spheres 70 estimate the location of cavity wall 48. In an embodiment, processor 41 locally maps tissue wall 48, by interpolating over segments 75.

The example illustration shown in FIG. 3 is chosen purely for the sake of conceptual clarity. For example, some of the spheres shown may not be to exact scale, for clarity of presentation. Segments 75 are, in reality, curves in space that extend in directions into, and out of, the page.

Figure 4:
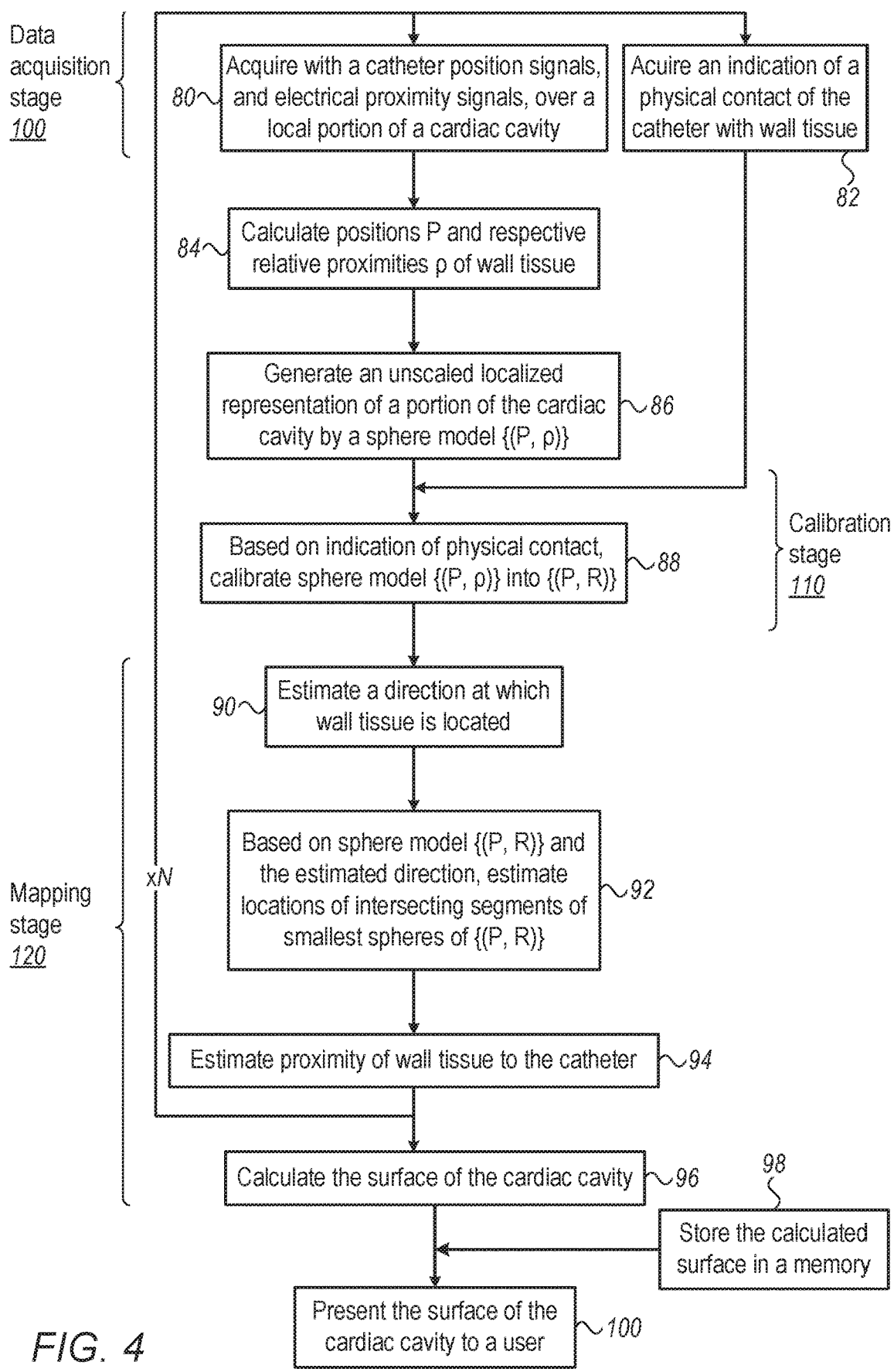
FIG. 4 is a flow chart that schematically illustrates a method for electro-anatomical mapping of a cardiac cavity, in accordance with an embodiment of the present invention.

FIG. 4 is a flow chart that schematically illustrates a method for electro-anatomical mapping of a cardiac cavity, in accordance with an embodiment of the present invention. In some embodiments, the steps of this algorithm are carried out by software with which processor 41 is programmed.

Data Acquisition Stage 100 (Steps 80-82)

The process begins with physician 30 moving catheter 40, which is equipped with magnetic sensor 50, inside a cardiac cavity to acquire multiple magnetic position signals and bi-polar electrical proximity signals, at a proximity data acquisition step 80.

In parallel, catheter 40, which comprises means to detect physical contact with the cardiac cavity wall, occasionally indicates to processor 41 of a physical contact that catheters 40 make with wall tissue, at an acquire physical contact indication step 82.

Based on the position signals and respective proximity signals, and using the dedicated algorithm, processor 41 calculates positions and respective relative (i.e., unscaled) proximities, at a position and unscaled proximity calculation step 84. Next, processor 41 represents a portion of the cardiac cavity with spheres $\{(P, \rho)\}_T$, at a local sphere-model construction step 86.

Calibration Stage 110

Next, based on indication of physical contact in the vicinity, i.e., at step 82, processor 41 calibrates the sphere-model into a model of spheres of known radius, $\{(P, R)\}_T$, at a calibration step 88.

Mapping Stage 120

Next, based on the local scaled sphere-model $\{(P, R)\}_T$, processor 41 estimates a direction at which wall tissue is located, by determining a direction 77 along which radiuses R become smaller, at a wall tissue direction estimation step 90.

Then, processor 41 estimates locations of intersecting segments 75 of the smallest spheres $\{(P, R)\}_T$, so as to estimate the location of cavity wall 48, at a tissue wall identification step 92. Based on cavity wall 48 identification step, processor 41 estimates proximity (i.e., distance) of cavity wall tissue 48 from catheter 40.

As noted above, the estimated tissue proximity is local. To produce an anatomical map of the cavity, the process described in steps 80-94 is typically repeated N times as the catheter moves inside the cavity. Next, at a cavity mapping step 96, based on the N collected proximities, processor 41 calculates a surface of the cardiac cavity. The calculated surface is stored in memory 47, at a storing step 98. Finally, at a cavity map displaying step 100, processor 41 presents to physician 30 the calculated surface (e.g., proximity map 31 of at least a portion of the cavity) on display 27.

The example flow chart shown in FIG. 4 is chosen purely for the sake of conceptual clarity. In alternative embodiments, for example, an entire cavity is mapped with acquisition steps 80-82 repeating at multiple distinct locations T over the cardiac cavity wall, and with modeling steps 84-94 repeating, until a sufficient portion of the cavity wall is electro-anatomical mapped. In an embodiment, the processor interpolates over intersecting segments 75 in order to derive a locally continuous cavity wall.

Although the embodiments described herein mainly address cardiac applications, the methods and systems described herein can also be used in other medical applications, such as in neurology and nephrology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving, from a probe that comprises electrodes and is positioned inside a cavity in an organ of a patient, (i) proximity signals indicative of proximity of the electrodes to a wall of the cavity based upon impedance measurement, receiving the proximity signals comprises receiving bi-polar electrical signals exchanged between the electrodes at one or more frequency ranges including a higher range wherein impedance is substantially insensitive to tissue and a lower range wherein impedance is sensitive to tissue, and (ii) position signals indicative of positions of the electrodes within the cavity;
based on a combination of the proximity signals and the position signals, representing at least a portion of a volume of the cavity by a sphere model comprising multiple spheres;
calibrate the sphere model by scaling the proximity signals into absolute values based upon physical contact of the probe and a wall of the cavity;
calculating an estimated contour of the wall of the cavity based on the calibrated sphere model; and
presenting the estimated contour of the wall to a user.

2. The method according to claim 1, wherein calculating the estimated contour comprises identifying, in the sphere model, directions along which sizes of the spheres decrease monotonically, and calculating the estimated contour depending on the directions.

3. The method according to claim 1, wherein calculating the estimated contour comprises finding intersections between smallest-size spheres in the sphere model, and defining the estimated contour to contain the intersections.

4. The method according to claim 1, wherein representing the volume by the sphere model comprises scaling radiuses of the spheres based on a subset of the proximity signals and the position signals, which were produced while one or more of the electrodes were in physical contact with the wall of the cavity.

5. The method according to claim 4, wherein scaling the radiuses comprises scaling the radiuses of the spheres based on a known geometry of the probe.

6. A system, comprising:
an interface, configured to receive, from a probe that comprises electrodes and is positioned inside a cavity in an organ of a patient, (i) proximity signals indicative of proximity of the electrodes to a wall of the cavity based upon impedance measurements, receiving the proximity signals comprises receiving bi-polar electrical signals exchanged between the electrodes at one or more frequency ranges including a higher range wherein impedance is substantially insensitive to tissue and a lower range wherein impedance is sensitive to tissue, and (ii) position signals indicative of positions of the electrodes within the cavity; and
a processor, configured to:
represent at least a portion of a volume of the cavity by a sphere model comprising multiple spheres, based on a combination of the proximity signals and the position signals;
calibrate the sphere model by scaling the proximity signals into absolute values based upon physical contact of the probe and a wall of the cavity;
calculate an estimated contour of the wall of the cavity based on the calibrated sphere model; and
present the estimated contour of the wall to a user.

7. The system according to claim 6, wherein the processor is configured to calculate the estimated contour by identifying, in the sphere model, directions along which sizes of the spheres decrease monotonically, and calculating the estimated contour depending on the directions.

8. The system according to claim 6, wherein the processor is configured to calculate the estimated contour by finding intersections between smallest-size spheres in the sphere model, and defining the estimated contour to contain the intersections.

9. The system according to claim 6, wherein the processor is configured to represent the volume by the sphere model by scaling radiuses of the spheres based on a subset of the proximity signals and the position signals, which were produced while one or more of the electrodes were in physical contact with the wall of the cavity.

10. The system according to claim 9, wherein the processor is configured to scale the radiuses based on a known geometry of the probe.

* * * * *